United States Patent [19]

Barron

[11] Patent Number: 4,950,789

[45] Date of Patent: Aug. 21, 1990

[54] AROMATIC POLYALKYLENEOXY POLYAMINES CONTAINING AMIONCARBONYL OR AMINOTHIOCARBONYL MOIETIES AND A COMPATIBLE MIXTURE OF HIGH AND LOW MOLECULAR WEIGHT POLYOLS MADE THEREFROM

[75] Inventor: Benny G. Barron, Lake Jackson, Tex.

[73] Assignee: The Dow Chemical Company, Midland, Mich.

[21] Appl. No.: 301,780

[22] Filed: Jan. 25, 1989

[51] Int. Cl.$^5$ ............... C07C 233/11; C07C 275/24; C07C 275/28; C07C 275/62

[52] U.S. Cl. .......................... 564/22; 564/27; 564/38; 564/48; 564/55; 564/74; 564/153; 564/157

[58] Field of Search .............. 564/22, 27, 38, 48, 564/55, 74, 153, 157

[56] References Cited

U.S. PATENT DOCUMENTS

| | | | |
|---|---|---|---|
| 2,311,753 | 2/1943 | Howard et al. | 564/157 |
| 2,311,754 | 2/1943 | Howard et al. | 564/157 |
| 2,330,291 | 9/1943 | Kirby | 564/153 |
| 3,152,162 | 10/1964 | Fischer et al. | 560/334 |
| 3,471,444 | 10/1969 | Sherer et al. | 564/157 |
| 3,654,370 | 4/1972 | Yeakey | 564/480 |
| 4,002,598 | 1/1977 | Waddill et al. | 528/110 |
| 4,014,933 | 3/1977 | Boettger et al. | 564/447 |
| 4,153,581 | 5/1979 | Habermann | 502/329 |
| 4,178,427 | 12/1979 | Waddill et al. | 528/124 |
| 4,218,543 | 8/1980 | Weber et al. | 521/51 |
| 4,233,302 | 11/1980 | Martin-Smith et al. | 564/27 |
| 4,264,614 | 4/1981 | Clitherow et al. | 564/27 |
| 4,269,945 | 5/1981 | Vanderhider et al. | 521/159 |
| 4,279,911 | 7/1981 | Martin-Smith et al. | 564/27 |
| 4,297,444 | 10/1981 | Gilbert et al. | 521/160 |
| 4,303,780 | 12/1981 | Bellos | 564/38 |
| 4,317,819 | 3/1982 | Clitherow et al. | 564/27 |
| 4,374,210 | 2/1983 | Ewen et al. | 521/159 |
| 4,433,154 | 2/1984 | Hirai | 564/157 |
| 4,485,031 | 11/1984 | Olstowski et al. | 252/182 |
| 4,485,032 | 11/9184 | Olstowski et al. | 252/182 |
| 4,492,658 | 1/1985 | Bellos | 564/27 |
| 4,530,941 | 7/1985 | Turner et al. | 521/176 |
| 4,558,155 | 12/1985 | Shanklin, Jr. et al. | 564/27 |
| 4,686,242 | 8/1987 | Turner et al. | 521/137 |

FOREIGN PATENT DOCUMENTS 81701 6/1983 European Pat. Off. .

Primary Examiner—Maurice J. Welsh
Assistant Examiner—Rabon Sergent

[57] ABSTRACT

Aromatic polyalkyleneoxy polyamines which are the reaction products of an aminocarbonyl, a polyalkyleneoxy polyamine, and aromatic diamines are useful in reaction injection molding processes to enhance the physical properties of the products produced. In addition, the polyamines of this invention are also useful as compatiblilizing agents in RIM systems to compatibilize mixtures of high molecular weight and low molecular weight polyols.

11 Claims, No Drawings

AROMATIC POLYALKYLENEOXY POLYAMINES CONTAINING AMIONCARBONYL OR AMINOTHIOCARBONYL MOIETIES AND A COMPATIBLE MIXTURE OF HIGH AND LOW MOLECULAR WEIGHT POLYOLS MADE THEREFROM

BACKGROUND OF THE INVENTION

This invention relates to reaction injection molded polyurethanes, polyureas and polyurea/urethanes which are prepared using polyisocyanates and polyols. This invention also relates to compatible mixtures of high and low molecular weight polyols.

Reaction injection molded polyurea/urethanes are well-known in the art as described by F. Melvin Sweeney in *Reaction Injection Molding Machinery and Processes*, Marcel Dekker, Inc., 1987. The use of reaction injection molding (RIM) polyurethanes in the production of structural parts for automotive applications such as fenders, doors and body panels as well as in other applications such as computer housings, sports equipment and the like is well known.

RIM polyurea/polyurethane processes typically employ the reaction of polyisocyanate with a high equivalent weight polyhydroxyl-containing compound, optionally in the presence of a chain extender which is a low equivalent weight polyhydroxyl- or polyamine-containing compound as disclosed in U.S. Pat. Nos. 4,297,444 and 4,686,242.

U.S. Pat. No. 4,218,543 discloses a process for using specific aromatic polyamines as chain extenders in a one-shot process. These aromatic diamines are characterized as having alkyl groups in both positions ortho to one amino group and in at least one of the positions ortho to the second amino group. U.S. Pat. No. 4,374,210 discloses a similar process for the use of aromatic diamines wherein at least one of the positions ortho to each of the amino groups is substituted by a lower alkyl. One disadvantage of these processes is the limited type and number of aromatic polyamine compounds which correspond to the above descriptions.

The use of urea and certain hydrocarbyl-substituted ureas as compatibilizing agents for ethylene glycol RIM systems is disclosed in U.S. Pat. Nos. 4,485,031 and 4,485,032. However, in RIM applications, the use of urea has been associated with surface defects in the final RIM product. It would be desirable to form a compatible mixture of high and low molecular weight polyols, without resulting in surface defects in the final RIM product. It would also be desirable to expand the number of choices of aromatic polyamine compounds which may practicably be used in RIM processes.

SUMMARY OF THE INVENTION

The present invention is, in one aspect, an aromatic polyalkyleneoxy polyamine compound comprising
(1) at least one polyalkyleneoxy moiety;
(2) at least one aromatic moiety;
(3) at least one aminocarbonyl or aminothiocarbonyl moiety; and
(4) at least two primary amine end groups,
wherein each amine end group is separated from each aminocarbonyl or aminothiocarbonyl moiety by a polyalkyleneoxy or aromatic moiety: and each polyalkyleneoxy or aromatic moiety is separated from each polyalkyleneoxy or aromatic moiety by at least one aminocarbonyl or aminothiocarbonyl moiety. These aromatic polyalkyleneoxy polyamine compounds may also be used as component (C) of the third aspect of the invention.

In a second aspect, the present invention is a polyurea/urethane composition comprising the reaction product of at least one relatively high molecular weight active hydrogen-containing compound material, at least one polyisocyanate, and at least one of the above-mentioned aromatic polyalkyleneoxy polyamine compounds.

In a third aspect, the present invention is a compatible mixture comprising
(A) at least one relatively high molecular weight polyol having an average hydroxyl functionality of from about 2 to about 4 and an average molecular weight of at least about 1000;
(B) at least one relatively low molecular weight polyol having an average hydroxyl functionality of from about 2 to about 6 and a molecular weight of less than about 300; and
(C) an amine-terminated polyalkyleneoxy polyurea or polyalkyleneoxy polythiourea; wherein
(1) Components (A) and (B) are present in quantities such that the mixture without the presence of component (C) is an incompatible mixture; and
(2) component (C) is present in a quantity sufficient to render the mixture compatible.

Normally, particular low and high molecular weight polyols are incompatible when mixed. The term "incompatible" as used herein means that the composition upon storage at a temperature of at least 25° C. forms at least two distinct layers within less than 5 days. The term compatible means that the mixture remains a single phase at a temperature of about 25° C. for at least 5 days. It has been discovered that the use of polyalkyleneoxy polyureas or polyalkyleneoxy polythioureas in RIM systems utilizing mixtures of high and low molecular weight polyols compatibilizes the polyol mixture. Further, the aromatic polyalkyleneoxy polyamine compound of this invention may be used as a compatibilizing agent. It has been discovered that the use of the compatibilizing agent of this invention will compatibilize mixtures of high and low molecular weight polyols without resulting in surface defects in the final RIM product.

DETAILED DESCRIPTION OF THE INVENTION

The aromatic polyalkyleneoxy polyamine compounds of this invention are characterized as having at least one polyalkyleneoxy moiety, at least one aromatic moiety, at least two aminocarbonyl or aminothiocarbonyl moieties, and at least two primary amine end groups, wherein each polyalkyleneoxy or aromatic moiety is separated from each polyalkyleneoxy or aromatic moiety by at least one aminocarbonyl or aminothiocarbonyl moiety. The prefix "poly-" as used herein means "two or more." In one embodiment, the structure of this aromatic polyalkyleneoxy polyamine compound is represented by the formula:

$$H(NH-R^1-NH-Y)_a-(NH-R^2-NH-Y)-_n-(NH-R^2-NH)-(Y-NH-R^1-NH)_bH$$

wherein $R^1$ is separately in each occurrence a divalent aromatic moiety, and is preferably

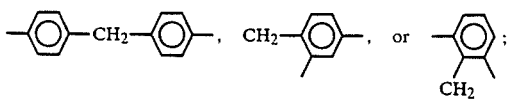

a and b are either 0 or 1, and $a+b \geq 1$; $R^2$ is separately in each occurrence a polyalkyleneoxy moiety, each Y is independently —C(O)—, —C(S)—, —C(O)NHC(O)—, —C(S)NHC(S)—, —C(O)$R^4$C(O)—, or —C(S)$R^4$C(S)—, wherein $R^4$ is separately in each occurrence a $C_{8-44}$ substituted or unsubstituted hydrocarbyl diradical; and n is a whole number between 0 and 10. Preferably, a and b are each 1 and/or n equals 0 or 1, since lower molecular weight materials are more suitable for use in RIM processes.

Preferably, the aromatic polyalkyleneoxy polyamine compounds of this invention are the reaction product of (a) a polyalkyleneoxy polyamine; (b) an aminocarbonyl, aminothiocarbonyl, or diacid compound; and (c) at least one aromatic diamine; which are combined at a reaction temperature sufficient to render the aromatic diamine in soluble form in the reaction mixture. These reactants may be combined in any order under any reaction conditions sufficient to produce the desired compound. However, in view of the higher reactivity of the polyalkyleneoxy polyamines relative to the aromatic diamines, it is advantageous to either partially react the aromatic diamine with the aminocarbonyl, aminothiocarbonyl, or diacid first and then add the polyalkyleneoxy polyamines to the reaction mixture, or to combine the amines first and then add the aminocarbonyl, aminothiocarbonyl, or diacid. The more preferred method is to combine the amines first before adding the aminocarbonyl, aminothiocarbonyl, or diacid. These preferred reaction methods are more likely to generate lower molecular weight materials which are more soluble and suitable for RIM applications.

In one embodiment of the preparation of the aromatic polyalkyleneoxy polyamine compound of this invention, aromatic diamines which are solid at room temperature are first heated with at least one polyalkyleneoxy polyamine until the aromatic diamines are in liquid form. Advantageously, this heating process is conducted at temperatures above about 100° C., more preferably above about 120° C., and most preferably above about 125° C. Preferably, this heating process is conducted at temperatures below about 220° C., more preferably below about 170° C., and most preferably below about 150° C. Preferred molar amounts range from a concentration of polyalkyleneoxy polyamine:aromatic diamine of about 1:1.5 to about 1:3.5. More preferably, the molar amounts range from about 1:1.9 to about 1:2.1. These preferred molar ranges enable the preparation of lower molecular weight aromatic polyalkyleneoxy polyamine compounds of the invention which are soluble in polyols.

Suitable aromatic amines include aromatic primary diamines such as 2,4-bis(p-aminobenzyl)aniline, 1,3-phenylenediamine, 1,4-phenylenediamine, naphthalene-1,5-diamine, 4,4'-di-(methylamino)diphenylmethane, 1-methyl-2-methylamino-4-aminobenzene, polyphenylpolymethylene diamines, 2,4-diaminomesitylene, 2,4-diaminotoluene, 2,6-diaminotoluene, 4,4'-methylene dianiline, 2,4'-methylene dianiline, or any mixture thereof may be utilized. Most preferred aromatic diamines are 2,4-diaminotoluene, 2,6-diaminotoluene, 4,4'-methylene dianiline, 2,4'-methylene dianiline, or any mixture thereof. An example of a commercial material which contains 4,4'-methylene dianiline is Curithane 103 TM diamine product, manufactured by The Dow Chemical Company. In one preferred embodiment, a mixture of 2,4- and 2,6-diaminotoluene and 4,4'-methylene dianiline is used. Most preferred, the diaminotoluene mixture and the 4,4'-methylene dianiline are present in molar amounts that range from about 0.8:1.2 to about 1.2:0.8. Preferably, the aromatic amines do not contain substituents which would sterically hinder their reaction with the aminocarbonyl or aminothiocarbonyl, such as, for example, diethyl toluenediamines. Such amines are more suitable for use as diluents for the reaction mixture.

Suitable polyalkyleneoxy polyamines include any one or more polyalkyleneoxy polyamines containing at least two primary amine groups, the preparation of which is described, for example, in U.S. Pat. No. 3,654,370. More preferred are polyoxypropylene diamines with a molecular weight ranging from about 200 to about 5000, more preferably from about 200 to about 2000, and most preferably from about 200 to about 800. In one preferred embodiment, the polyoxypropylene diamine employed has a molecular weight of about 400. An example of a commercial polyoxypropylene diamine of this type is Jeffamine TM D-400 diamine product, manufactured by Texaco Chemical Company.

In a preferred embodiment, the liquid amine mixture is then heated and mixed with at least one aminocarbonyl, aminothiocarbonyl, or diacid compound. Suitable materials include, for example, urea, biuret, carboxylic acid, thiourea, dithiobiuret, or thiocarboxylic acid. In one preferred embodiment, the aminocarbonyl compound employed is urea, since this is an inexpensive material and this embodiment will compatibilize mixtures of high and low molecular weight polyols. Preferred carboxylic acids are dimer acids, since these higher molecular weight dimerized unsaturated fatty acids will generate a more soluble aromatic polyalkyleneoxy polyamine compound than lower molecular weight diacids. Generally, this reaction process is conducted at temperatures above about 100° C., more preferably above about 120° C., and most preferably above about 130° C. Preferably, the reaction process is conducted at temperatures below about 220° C., more preferably below about 170° C., and most preferably below about 150° C.

In the most preferred embodiment, the aminocarbonyl or aminothiocarbonyl compound and aromatic amines are present in approximately equimolar amounts, since this leads to preferred embodiments of the claimed aromatic polyalkyleneoxy polyamine compound. However, preferred molar ratios of aromatic amine:aminocarbonyl range from about 2.1:0.9 to about 0.9:1.1, more preferably from about 1.1:0.9 to about 0.9:1.1.

When urea is used as the aminocarbonyl compound, ammonia is eliminated from the reaction mixture. Reduced pressure reaction conditions facilitate the removal of ammonia from the reaction mixture. In addition, suitable agents to reduce the viscosity of the reaction mixture may optionally be employed as a reaction medium. Preferred viscosity-reducing agents are high or low molecular weight polyols or sterically-hindered amines such as, for example, diethyl toluenediamines, since they are suitable for use in RIM formulations. Diethyl toluenediamines also serve as chain extenders in the RIM formulation to enhance the physical properties of the final RIM product.

In one preferred embodiment, a sterically-hindered aromatic amine such as 2,4- or 2,6-diethyl toluenediamine (DETDA) is added to the reaction mixture to reduce the viscosity of the aromatic polyalkyleneoxy polyamine product, since these sterically-hindered amines are very slow to react with the reaction components, and may also enhance the physical properties of the final RIM product. Preferred polyols for use as viscosity-reducing agents are those with primary hydroxyl groups, such as ethylene glycol or 1,4-butanediol, since they are more highly reactive in RIM formulations. Ethylene glycol is the most preferred viscosity-reducing agent, since it does not react with the urea and amines in the reaction mixture and also serves as a chain extender in many RIM formulations.

The second aspect of this invention is a polyurea/urethane composition comprising the reaction product of a reaction mixture comprising at least one relatively high molecular weight active hydrogen-containing compound material, at least one polyisocyanate, and at least one of the above-mentioned aromatic polyalkyleneoxy polyamine compounds. The relatively high molecular weight active hydrogen-containing compound materials which can be employed herein are di- or greater functionality high molecular weight alcohols or amine-terminated polyethers. The high molecular weight alcohols suitable for use in this invention are those which have an average hydroxyl functionality of from about 1.8 to about 8, preferably from about 2 to about 4 and an average hydroxyl equivalent weight preferably above about 500, more preferably above about 700, most preferably above about 1000; and preferably below about 5000, more preferably below about 3000, and most preferably below about 2000, including mixtures thereof.

Polyether polyols are preferred high molecular weight alcohols for the process of the present invention. These polyether polyols may be prepared by any known method and include, for example, polyoxyethylene and polyoxypropylene diols and triols having equivalent weights in the above-stated ranges which are obtained by reacting an unsubstituted or halogen- or aromatic-substituted alkylene oxide with an initiator compound containing two or more active hydrogens such as water, ammonia, polyalcohol, or an amine. See, for example, U.S. Pat. Nos. 4,269,945, 4,218,543, and 4,374,210, the relevant portions of which are hereby incorporated by reference. Most preferred, however, are ethylene oxide-capped polyols prepared by reacting glycerine with propylene oxide, followed by reacting with ethylene oxide. These polyols have a high primary hydroxyl functionality, which makes them the most preferred for RIM applications. Hydroxyl-containing polyesters, polythioethers, polyacetals, polycarbonates, or polyester amides which have functionalities and equivalent weights in the above-stated ranges for polyether polyols and are useful for the production of polyurea/urethanes may also be used instead of or together with polyether polyols.

The high molecular weight amine-terminated polyethers useful in this invention are those which have an average amine functionality of from about 1 to about 4, preferably from about 2 to about 3 and an average amine equivalent weight of from about 100 to about 3000, preferably from about 200 to about 2500, most preferably from about 1000 to about 2000, including mixtures thereof. These amine-terminated polyethers include the above-mentioned polyether polyols which are modified to contain a proportion of primary or secondary amine groups, preferably from about 30 percent to about 100 percent of the total number of amine and hydroxy functional groups.

These amine-terminated polyethers may be prepared by a variety of known methods. For example, a polyether polyol may be reacted with a primary amine and then reduced with hydrogen, as described in U.S. Pat. No. 4,153,581. Second, secondary amine-terminated compounds can be prepared in a Michaels addition reaction of the corresponding primary aliphatic amine with an ethylenically unsaturated compound. In a third method, a polyether polyol may be reacted with ammonia to form the amine-terminated polyether. For ease of amination, it is preferred that the hydroxyl groups in the polyol be essentially all secondary hydroxyl groups. See, e.g., U.S. Pat. Nos. 3,654,370 and 4,014,933, the relevant portions of which are hereby incorporated by reference.

The aromatic polyalkyleneoxy polyamine compound as prepared above can be optionally combined with additional chain extenders before they are mixed with the polyol. Suitable additional chain extenders which may be employed herein include hydroxyl-containing chain extenders, aliphatic amine-containing chain extenders, and aromatic amine chain extenders. Examples of suitable chain extenders are listed in U.S. Pat. No. 4,269,945, the relevant portions of which are hereby incorporated by reference. Additional suitable aromatic amines are listed in U.S. Pat. No. 4,374,210. Preferred hydroxyl-containing chain extenders are low molecular weight polyols such as alkylene glycols for the tensile strength improvements gained by their use in particular RIM applications. In the most preferred embodiment, ethylene glycol is used as the chain extender. If the chain extender is also used as a viscosity-reducing agent in the aromatic polyalkyleneoxy polyamine reaction mixture, reaction conditions resulting in the boiling of the ethylene glycol will facilitate removal of the ammonia produced in the reaction.

Suitable polyisocyanates include aliphatic or aromatic polyisocyanates or mixtures thereof. For example, any polyisocyanate having 2 or more NCO groups per molecule may be used. Aromatic polyisocyanates are preferred for their suitability in RIM applications. Examples of such compounds include toluene-2,4- and -2,6-diisocyanate, 2,2'-, 2,4'-, and 4,4'-methylene bis(phenyl isocyanate), and mixtures of these isomers. In addition, prepolymers of aliphatic and aromatic isocyanates, sometimes referred to as "liquid isocyanates", such as those containing urethane, carbodiimide, allophanate, isocyanurate, acylated urea, biuret, ester and similar groups, may also be used. These prepolymers may be prepared by reacting the polyisocyanates with aliphatic polyhydroxyl compounds in the molecular weight range of about 50 to about 6000 such as $C_{2-10}$ alkylene glycols, as illustrated in U.S. Pat. No. 4,374,210 and EPO Application No. 81,701, the relevant portions of which are incorporated by reference.

The preferred isocyanates include the derivatives of 4,4'-methylene bis(phenyl isocyanate) which are liquid at room temperature such as, for example, polyisocyanates which have carbodiimide groups in their backbone or mixtures thereof, the preparation of which is disclosed in U.S. Pat. No. 3,152,162. These "Liquid MDI" products are of particular significance for their suitability in RIM applications. An example of a commercial material of this type is Isonate ™ 143L Isocyanate, a product of The Dow Chemical Company. Mixtures of prepolymers and Liquid MDI products are also preferred isocyanates. An example of a commercial material of this type is Spectrim ™ 5A Isocyanate, a product of The Dow Chemical Company.

The polyurea/urethane products of this invention can optionally be prepared in the presence of blowing agents, coloring agents, mold release agents, fillers, or fire-retardant agents which are well-known in the art and are described, for example, in U.S. Pat. No. 4,269,945, the relevant portions of which are hereby incorporated by reference. In addition, any of the catalysts which are known to catalyze the reaction of an isocyanate with an active hydrogen-containing compound may optionally be employed. Suitable catalysts are described in U.S. Pat. Nos. 4,269,945 and 4,374,210. In one preferred embodiment, the catalysts employed are commonly available organotin catalysts such as, for example, dioctyltin dilaurate.

The polyurea/urethane composition mentioned above and in the following examples may be processed into a polyurea/urethane by any suitable known technique. Suitable techniques are described, for example, in U.S. Pat. Nos. 4,218,543 and 4,269,945. The moldings obtainable from such processes are particularly suitable for the manufacture of flexible car bumpers and car body elements.

In the third aspect of this invention, a compatibilizing agent is used to compatibilize an ordinarily incompatible mixture of relatively low molecular weight and relatively high molecular weight polyols. The term incompatible as used herein means that the composition upon storage at a temperature of at least about 25° C. forms at least two distinct layers within less than 5 days. The term compatible means that the mixture remains a single phase at a temperature of at least about 25° C. for at least 5 days.

The compatibilizing agent of this invention, which is optionally comprised of the aromatic polyalkyleneoxy polyamine compound of the invention, is a polyalkyleneoxy polyurea polyamine or polyalkyleneoxy polythiourea polyamine. This polyamine preferably contains aromatic substituents and more preferably is the aromatic polyalkyleneoxy polyamine compound of this invention previously described, since such provides enhancement of the physical properties of the RIM product. The low molecular weight polyol may be compatibilized in the high molecular weight polyol by adding the compatibilizing agent of this invention in amounts sufficient to render the mixture of high and low molecular weight polyols compatible.

This agent is preferably prepared by reacting polyalkyleneoxy polyamines with materials which will produce an aminocarbonyl or aminothiocarbonyl linkage, such as the aminocarbonyls, aminothiocarbonyls, or diacids mentioned previously, optionally in the presence of aromatic diamines. Materials prepared by reacting polyalkyleneoxy polyamines with materials which will produce an aminocarbonyl or aminothiocarbonyl linkage are disclosed in Harris et al., "Amino-Functional Polyethers Containing Urea, Biuret, Thiourea, Dithiobiuret, Thioamide, and/or Amide Moieties in Their Backbone and Urethane/urea Prepolymers and Polymers Made Therefrom," copending application Ser. No. 247,460. In addition, polyurea polyamines used as epoxy curing agents are disclosed in U.S. Pat. Nos. 4,178,427 and 4,002,598. This agent is formed by the reaction of a polyoxypropylene polyamine with urea.

The relatively high molecular weight polyols are the relatively high molecular weight alcohols previously described. The term "molecular weight" as used herein refers to the molecular weight of the material as may be determined by gel permeation chromatography. The relatively low molecular weight polyols mentioned above have an average hydroxyl functionality of from about 2 to about 6, more preferably from about 2 to about 4, and a molecular weight of less than about 1000, preferably from about 60 to about 600. Preferred low molecular weight polyols are $C_{2-12}$ alkylene glycols; more preferred are $C_{2-4}$ alkylene glycols. Most preferred is ethylene glycol, due to the enhancement of physical properties gained by its use in RIM formulations, as mentioned above.

The compatibilized mixture of high and low molecular weight polyols may be processed into a polyurea/urethane by any suitable known technique, as described above.

ILLUSTRATIVE EMBODIMENTS

The following examples are given to illustrate the invention and should not be interpreted as limiting it in any way. Unless stated otherwise, all parts and percentages are given by weight.

EXAMPLE 1

In a suitable reaction vessel, 2.5 moles of 4,4'-methylene dianiline (MDA) and 2.5 moles of urea are mixed and heated to 140° C. Jeffamine ™ D-400 diamine product (1.625 moles) (a polyalkyleneoxy diamine with a molecular weight of approximately 400) is then added in several portions over a 2-hour period during which the reaction temperature is raised to 150° C. The reaction temperature is then increased to 160° C. and a light vacuum applied to facilitate removal of the evolving ammonia. After 5 hours total reaction time from the time urea was first added to the reaction mixture, 2.25 moles of diethyl toluenediamine are added to reduce viscosity. Heating under reduced pressure is continued for one hour. The liquid product is then cooled to 100° C. under vacuum. Perchloric titration gives 5.498 meq/g or 181.9 amine eq. wt. Gel Permeation Chromatography based on a calibration using glycerine-initiated polypropoxide triols indicates polyurea diamine molecular weight average sizes of 1291. Residual unreacted MDA is also present. The preferred product of this example has the following structure:

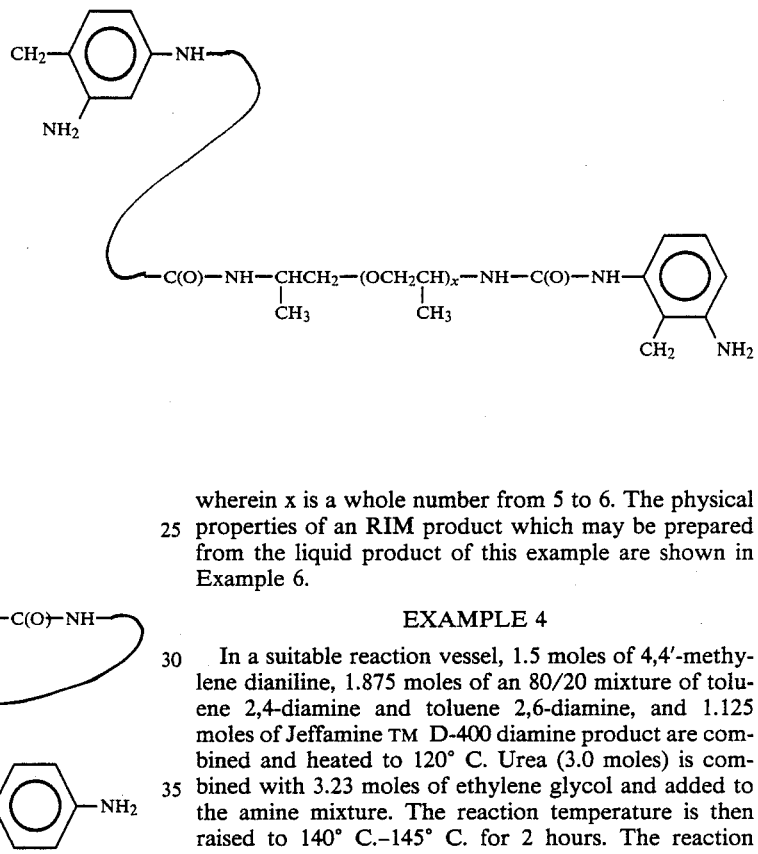

wherein x is a number between 5 and 6 and y is a number between 1 and 2. The physical properties of an RIM product which may be prepared from the liquid product of this example are shown in Example 6.

EXAMPLE 2

In a suitable reaction vessel, 2.5 moles of 4,4'-methylene dianiline, 1.25 moles of Jeffamine TM D-400 diamine product, and 2.5 moles of urea are reacted at 143° C. for 1.5 hours. Ethylene glycol (4.8 moles) is then added to reduce the viscosity of the reaction mixture as the reaction temperature is maintained. After 1 hour, an additional 3.265 moles of ethylene glycol is added under partial vacuum. Total reaction time is about 7 hours at 143° C. The preferred product of this example has the same structure as that of Example 1. The physical properties of an RIM product which may be prepared from the liquid product of this example are shown in Example 6.

EXAMPLE 3

In a suitable reaction vessel, 2.5 moles of an 80/20 mixture of toluene 2,4-diamine and toluene 2,6-diamine and 1.25 moles of Jeffamine TM D-400 diamine product are combined and heated to 135° C. Urea (2.5 moles) is combined with 3.2 moles of ethylene glycol and added to the amine mixture. The reaction temperature is then increased to 140° C.–145° C. and an additional 1.64 moles of ethylene glycol is added to the reaction mixture. After 4 hours, the reaction pressure is reduced to 110 mm Hg to remove ammonia. The product is cooled after 1 hour. The preferred product of this example has the following structure:

wherein x is a whole number from 5 to 6. The physical properties of an RIM product which may be prepared from the liquid product of this example are shown in Example 6.

EXAMPLE 4

In a suitable reaction vessel, 1.5 moles of 4,4'-methylene dianiline, 1.875 moles of an 80/20 mixture of toluene 2,4-diamine and toluene 2,6-diamine, and 1.125 moles of Jeffamine TM D-400 diamine product are combined and heated to 120° C. Urea (3.0 moles) is combined with 3.23 moles of ethylene glycol and added to the amine mixture. The reaction temperature is then raised to 140° C.–145° C. for 2 hours. The reaction pressure is then reduced to 110 mm Hg for 2 hours. Ethylene glycol (6.45 moles) is added and the reaction mixture is cooled under vacuum. The preferred structure of the product of this example is as follows:

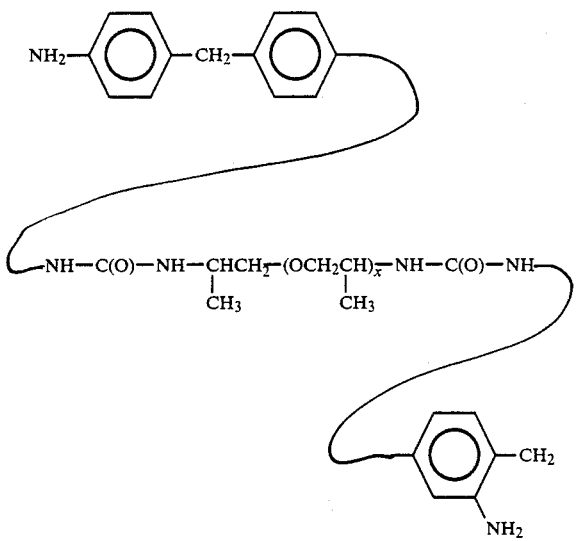

wherein x is a whole number from 5 to 6. The physical properties of an RIM product which may be prepared from the liquid product of this example are shown in Example 6.

EXAMPLE 5

In a suitable reaction vessel, 1.5 moles of an 80/20 mixture of toluene 2,4-diamine and toluene 2,6-diamine, 1.5 moles of Jeffamine TM D-400 diamine product, 3 eq. wt. of Curithane TM 103 diamine product (manufactured by The Dow Chemical Company), and 3.2 moles of ethylene glycol are combined and heated to 135° C. Urea (3.0 moles) is added in portions over a 45-minute period. Ethylene glycol (1.64 moles) is then added and the reaction continued for 2 hours at 140° C. Reduced pressure is applied to remove the ammonia. After 4.25 hours total reaction time, the ethylene glycol will be refluxing at 140° C. and 80 mm Hg. These reaction conditions are maintained an additional 2.75 hours. The product is then cooled. The preferred product is the same as for Example 4. The physical properties of an RIM product which may be prepared from the liquid product of this example are shown in Example 6.

EXAMPLES 6a–j and 7a–g

The polyurea diamines prepared in Examples 1–6 may be used in ethylene glycol-extended RIM fascia formulations. These formulations may be run on a Hi-Tech mini-RIM apparatus to obtain 6×6×⅛ in. plaques for physical property testing. Formulations, as well as obtainable physical property data, are presented in the following tables. Spectrim TM 5A Isocyanate, with an NCO equivalent weight of about 165, is used as the A-side isocyanate. A glycerine-based polyoxypropylene triol, capped with 19.6 percent ethylene oxide to give a molecular weight of about 4935 is used as the polyether polyol. All B-side polyol formulations are compatible. All formulations are given in weight percent. The amounts of ethylene glycol and diethyl toluenediamine (DETDA) shown include amounts added to the reaction mixtures in Examples 1–6. Plaques are demolded after 30–40 seconds.

TABLE I

|  | Comp. Exam. 6a* | Comp. Exam. 6b* | 6c | 6d | 6e | 6f | 6g | 6h | 6i | 6j |
|---|---|---|---|---|---|---|---|---|---|---|
| B-side, % |  |  |  |  |  |  |  |  |  |  |
| polyether polyol | 87.3 | 76.39 | 77.44 | 69.12 | 70.13 | 60.06 | 70.14 | 60.84 | 59.90 | 59.90 |
| Example 1 |  |  | 11.11 | 11.33 |  |  |  |  |  |  |
| Example 2 |  |  |  |  | 12.48 | 20.44 |  |  |  |  |
| Example 3 |  |  |  |  |  |  | 13.65 | 19.59 |  |  |
| Example 4 |  |  |  |  |  |  |  |  | 20.00 |  |
| Example 5 |  |  |  |  |  |  |  |  |  | 20.00 |
| ethylene glycol | 10.0 | 18.72 | 7.59 | 15.63 | 17.18 | 19.32 | 16.01 | 19.42 | 20.00 | 20.00 |
| urea | 2.5 | 4.62 |  |  |  |  |  |  |  |  |
| DETDA |  |  | 3.67 | 3.75 |  |  |  |  |  |  |
| UL-38** | 0.20 | 0.21 | 0.18 | 0.18 | 0.19 | 0.16 | 0.19 | 0.17 | 0.10 | 0.10 |
| B/A Ratio (by weight) | 1.558 | 0.907 | 1.624 | 0.951 | 0.941 | 0.833 | 0.983 | 0.892 | 0.837 | 0.804 |

*Not an example of this invention. Comparative Examples 6a and 6b show a RIM formulation without the use of the compounds of this invention.
**Fomrez TM UL-38 is a dioctyltin dilaurate catalyst made by Witco.

TABLE II

|  | Comp. Exam. 6a* | Comp. Exam. 6b* | 6c | 6d | 6e | 6f | 6g | 6h | 6i | 6j |
|---|---|---|---|---|---|---|---|---|---|---|
| tensile strength, psi | 2467 | 4105 | 3152 | 4405 | 4014 | 4512 | 5325 | 4457 | 4651 | 4935 |
| elongation, % | 248 | 271 | 223 | 152 | 46 | 15 | 160 | 135 | 53 | 41 |
| flexural modulus, psi | 6339 | 73452 | 21909 | 116071 | 114203 | 146752 | 102437 | 140568 | 171665 | 159287 |
| flexural strength, psi | 296 | 3045 | 929 | 4747 | 4450 | 5865 | 4157 | 5612 | 6880 | 6276 |
| Heat sag, 4 in, mm |  |  |  |  |  |  |  |  |  |  |
| 200° F. | 10.7 | 9.7 | 26 | 11 | 18 | 11.7 | 30 | 37 | 28 |  |
| 250° F. | 19.7 |  | 52 | 12 |  |  |  |  |  | 25.3 |
| tear strength, "C", pli | 343 | 692 | 440 | 816 | 781 | 640 | 890 | 954 | 999 | 996 |
| notched Izod, in-lb |  |  |  |  |  |  |  |  |  |  |
| 77° F. |  |  |  |  | 64 | 43 | 128 | 37 | 84 | 85.1 |
| −20° F. |  |  |  |  | 21 | 16 | 19 | 20 | 15 | 25.5 |

*Not an example of this invention. Comparative Examples 6a and 6b show a RIM formulation without the use of the compounds of this invention.

TABLE III

|  | 7a | 7b | 7c | 7d | 7e | 7f | 7g |
|---|---|---|---|---|---|---|---|
| B-side, % |  |  |  |  |  |  |  |
| polyether polyol | 87.8 | 88.3 | 87.3 | 89.8 | 90.3 | 85.8 | 89.8 |
| Example 5 compound | 2 | 1.5 | 2.5 | 2 | 1.5 | 2 | 4 |
| ethylene glycol | 10 | 10 | 10 | 8 | 8 | 12 | 6 |
| UL-38 | 0.2 | 0.2 | 0.2 | 0.2 | 0.2 | 0.2 | 0.2 |
| B/A Ratio | 1.5021 | 1.5179 | 1.4866 | 1.7918 | 1.8144 | 1.2930 | 2.091 |
| specific gravity | 1.048 | 1.044 | 1.028 | 0.997 | 1.012 | 1.037 | 0.996 |
| tensile strength, psi | 2879 | 2887 | 2802 | 2139 | 2090 | 3144 | 2015 |
| elongation, % | 294 | 282 | 274 | 259 | 257 | 265 | 297 |

TABLE III-continued

|  | 7a | 7b | 7c | 7d | 7e | 7f | 7g |
|---|---|---|---|---|---|---|---|
| flexural modulus, psi | 6739 | 6278 | 6942 | 3246 | 3538 | 14198 | 2463 |
| tear strength, "C", pli | 379 | 386 | 384 | 270 | 280 | 437 | 239 |

The data shown in Table 2 shows that the use of the aromatic diamine of this invention as a compatibilizing agent results in improved physical properties of the final RIM product. For example, the data shown for Examples 6e–j, which contain a comparable level of ethylene glycol to that of Comparative Example 6b, show significant increases in the tensile strength, flexural modulus, flexural strength, and tear strength of a RIM product containing the aromatic diamines of the invention over the RIM product of Example 6b. The data shown in Table 3 shows the variety of physical properties obtainable by varying the amounts of the components of the B-side formulation when the product of Example 5 is used.

What is claimed is:

1. An aromatic polyalkyleneoxy polyamine compound comprising
   (1) at least one polyalkyleneoxy moiety:
   (2) at least one aromatic moiety;
   (3) at least one aminocarbonyl or aminothiocarbonyl moiety: and
   (4) at least two primary amine end groups,
wherein each amine end group is separated from each aminocarbonyl or aminothiocarbonyl moiety by a polyalkyleneoxy or aromatic moiety; and each polyalkyleneoxy or aromatic moiety is separated from each polyalkyleneoxy or aromatic moiety by at least one aminocarbonyl or aminothiocarbonyl moiety.

2. The aromatic polyalkyleneoxy polyamine compound of claim 1 which is represented by the following formula:

H(NH—R$^1$—NH—Y)$_a$—(NH—R$^2$—NH—Y)$_n$—(NH—R$^2$—NH)—(Y—NH—R$^1$—NH)$_b$H wherein R$^1$ is separately in each occurrence an aromatic moiety, a and b are either 0 or 1, and a+b≧1; R$^2$ is separately in each occurrence a polyalkyleneoxy moiety, each Y is independently —C(O)—, —C(S)—, —C(O)NHC(O)—, —C(S)NHC(S)—, —C(O)R$^4$C(O)—, or —C(S)R$^4$C(S)—, wherein R$^4$ is separately in each occurrence a C$_{8-44}$ substituted or unsubstituted hydrocarbyl radical; and n is a whole number between 0 and 10.

3. The aromatic polyalkyleneoxy polyamine compound of claim 2 wherein Y is —C(O)—.

4. The aromatic polyalkyleneoxy polyamine compound of claim 2 wherein R$^1$ is selected from the group comprising:

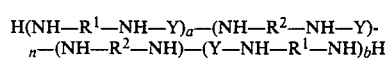

5. The aromatic polyalkyleneoxy polyamine compound of claim 1 which comprises the reaction product of a polyalkyleneoxy polyamine; an aminocarbonyl, aminothiocarbonyl, or diacid; and at least one aromatic diamine.

6. The aromatic polyalkyleneoxy polyamine compound of claim 4 wherein the polyalkyleneoxy polyamine is a polyalkyleneoxy diamine.

7. The aromatic polyalkyleneoxy polyamine compound of claim 4 wherein the aminocarbonyl is urea.

8. The aromatic polyalkyleneoxy polyamine compound of claim 4 wherein the diacid is a dimer acid.

9. The aromatic polyalkyleneoxy polyamine compound of claim 4 wherein the aromatic diamine is toluene diamine.

10. The aromatic polyalkyleneoxy polyamine compound of claim 4 wherein the aromatic diamine is 4,4'-methylene dianiline.

11. The aromatic polyalkyleneoxy polyamine compound of claim 4 wherein the aromatic diamines comprise a combination of 2,4- and 2,6-toluene diamine and 4,4'-methylene dianiline.

* * * * *